US006271231B1

(12) United States Patent
Bergstrand et al.

(10) Patent No.: US 6,271,231 B1
(45) Date of Patent: Aug. 7, 2001

(54) PHARMACEUTICALLY ACTIVE COMPOUNDS

(75) Inventors: Håkan Bergstrand, Bjärred; Kostas Karabelas; Peter Sjö, both of Lund, all of (SE)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 08/981,266

(22) PCT Filed: Sep. 19, 1997

(86) PCT No.: PCT/SE97/01582

§ 371 Date: Dec. 12, 1997

§ 102(e) Date: Dec. 12, 1997

(87) PCT Pub. No.: WO98/13368

PCT Pub. Date: Apr. 2, 1998

(30) Foreign Application Priority Data

Sep. 25, 1996 (SE) .................................................. 9603505
Jul. 18, 1997 (SE) .................................................. 9702747

(51) Int. Cl.$^7$ .................. A61K 31/498; A61K 31/4985; C07D 403/04; C07D 471/04

(52) U.S. Cl. .......................... 514/249; 514/250; 544/344; 544/350; 544/354; 544/257; 548/455; 548/468

(58) Field of Search .............................. 544/359; 514/249

(56) References Cited

U.S. PATENT DOCUMENTS

| Re. 28,973 | 9/1976 | Welstead, Jr. ............. 260/293.61 |
| 3,056,784 | * 10/1962 | Carr, Jr. et al. .................. 544/354 |
| 3,642,803 | 2/1972 | Welstead, Jr. ............. 260/293.61 |
| 3,821,389 | 6/1974 | Grivas ................................. 424/270 |
| 4,031,221 | 6/1977 | Helsley et al. ................... 424/267 |
| 4,062,869 | 12/1977 | Weston ......................... 260/326.16 |
| 4,598,079 | 7/1986 | Beyerle et al. ................... 514/252 |
| 5,057,614 | 10/1991 | Davis et al. ..................... 548/466 |
| 5,077,293 | 12/1991 | Smith et al. ..................... 514/253 |
| 5,192,770 | 3/1993 | Clark et al. ...................... 514/305 |
| 5,380,746 | 1/1995 | Barth et al. ...................... 514/414 |
| 5,399,712 | 3/1995 | Hill ................................... 578/455 |
| 5,516,915 | 5/1996 | Barth et al. ..................... 548/455 |
| 5,545,636 | 8/1996 | Heath et al. ..................... 514/214 |

FOREIGN PATENT DOCUMENTS

| 0 464 604 A2 | 1/1992 | (EP) . |
| 0 490 263 A1 | 6/1992 | (EP) . |
| 0 540 956 A1 | 11/1993 | (EP) . |
| 0 675 125 A1 | 10/1995 | (EP) . |
| 73 11450 | 3/1973 | (FR) . |
| 1 500 176 | 2/1978 | (GB) . |
| WO 93/18765 | 9/1993 | (WO) . |
| WO 95/17182 | 6/1995 | (WO) . |
| WO 96/01825 | 1/1996 | (WO) . |
| WO 98/13368 | 4/1998 | (WO) . |

OTHER PUBLICATIONS

Bergstrand et al., "Modulation of Neutrophil Superoxide Generation by Inhibitors of Protein Kinase C, . . . " The Journal of Pharmacology and Experimental Therapeutics, vol. 263, No. 3, pp. 1334–1346.

Chakravarthy et al., "The Direct Measurement of Protien Kinase C (PKC) Activity in Isolated Membranes Using a Selective Peptide Substrate", Analytical Biochemistry, 1991, vol. 196, pp. 144–150.

Gazit et al., "Tyrphostins. 5. Potent Inhibitors of Platelet–Derived growth Factor Receptor Tyrosine Kinase: Structure–Activity Relationships . . . ", J. Med. Chem., 1996, vol. 39, pp. 2170–2177.

Granet et al., "A Microtiter Plate Assay for Protein Kinase $C^{1}$", Analytical Biochemistry, 1987, vol. 163 pp. 458–463.

Olsson et al., Activation of Human Neutrophil Protein Kinase C in vitro by 1,2–isopropylidene–3–decanoyl–sn–glycerol ($IpOCOC_9$), Cellular Signalling, 1989, vol. 1, No. 4, pp. 405–410.

Glazunov et al., "Investigation of the Riboflavine Operon of *Bacillus subtilis* VII. Biochemical Study of Mutants Relating to Early Stages of Biosynthesis" Translated from Genetika 10(11):83–92, 1974, see Chemical Abstracts vol. 82 No. 13 (1975) abstract 82817b.

Cook et al., *J. Chem. Soc.* p397–400 (1943).*

Rossi et al. Chemical Abstracts, vol. 55, No. 15456f (1961).*

Kollenz, Chemical Abstracts, vol. 78, No. 16132 (1973).*

Chupakhin et al., Chemical Abstracts, vol. 84, No. 43979 (1976).*

Dormidontov et al., Chemical Abstracts, vol. 87, No. 135251 (1977).*

* cited by examiner

Primary Examiner—Emily Bernhardt
(74) Attorney, Agent, or Firm—Fish & Richardson P.C.

(57) ABSTRACT

The present invention provides optionally substituted and/or annulated compounds of formula (I)

(I)

wherein X, Y, Z and A is each independently carbon or nitrogen, and at least two of X, Y, Z and A are carbon; and pharmaceutically acceptable salts thereof with the proviso that:

3-(1H-Indol-3-yl)-1H-quinoxalin-2-one,
3-(2-Methyl-1H-indol-3-yl)-1H-quinoxalin-2-one, and
3-(1,2-Diphenyl-1H-indol-3-yl)-1H-quinoxalin-2-one are excluded from compounds of formula (I). The invention includes the use of compounds of formula (I) in medical therapy, particularly in the therapy of conditions requiring inhibition of protein kinase C.

11 Claims, No Drawings

PHARMACEUTICALLY ACTIVE COMPOUNDS

This is a continuation of International Patent Application No. PCT/SE97/01582, with an international filing date of Sep. 19, 1997, now pending.

The present invention relates to novel compounds which are protein kinase C inhibitors, methods for their preparation, intermediates therefor and pharmaceutical compositions comprising them.

Protein kinase C (PKC) is a family of phospholipid-dependent serine/threonine-specific protein kinases which play an important role in cellular growth control, regulation and differentiation.

Since the activation of PKC has been implicated in several human disease processes, including various forms of cancer, different forms of inflammatory and/or immunological disorders as well as some neurological disorders, inhibition of PKC could be of therapeutic value in treating these conditions.

Several classes of compounds have been identified as PKC inhibitors, e.g. isoquinoline sulphonarnides, sphingosine and related sphingolipids, indolocarbazoles and bis-indolylmaleimides.

Although PKC inhibitors are described in the prior art, there is a need for specific anti-inflammatory and immunosuppressive compounds which are suitable for oral administration, and for inhalation.

The present invention provides PKC inhibitors, methods for their preparation and intermediates used for their preparation.

The present invention also provides the use of the compounds of the present invention for the treatment of inflammatory, immunological, bronchopulmonary, cardiovascular, oncological or CNS-degenerative disorders.

Also provided by the present invention are pharmaceutical compositions comprising a compound according to the present invention, as active ingredient, together with a pharmaceutically acceptable adjuvant, diluent or carrier.

The present invention provides optionally substituted and/or annulated compounds of formula (I)

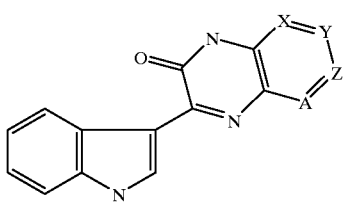

(I)

wherein X, Y, Z and A is each independently carbon or nitrogen, and at least two of X, Y, Z and A are carbon;

and pharmaceutically acceptable salts thereof with the proviso that the following compounds are not included in formula (I):

3-(1H-Indol-3-yl)-1H-quinoxalin-2-one,
3-(2-Methyl-1H-indol-3-yl)-1H-quinoxalin-2-one, and
3-(1,2-Diphenyl-1H-indol-3-yl)-1H-quinoxalin-2-one.

Preferred compounds of formula (I) are those of formula (IA):

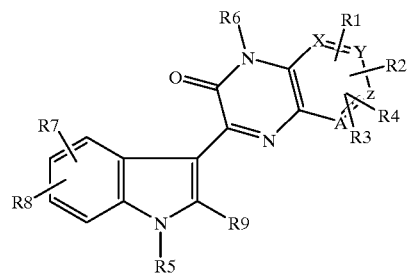

(IA)

wherein X, Y, Z and A are as defined above, $R_1$, $R_2$, $R_3$, and $R_4$ is each independently H, hydroxy, amino, nitro, halo, $C_{1-6}$ alkyl, phenyl$C_{1-6}$ alkyl, $C_{1-6}$ alkoxy, halo$C_{1-6}$ alkyl, carboxy$C_{1-6}$ alkyl ester or $R_1$ and $R_2$ or $R_2$ and $R_3$ or $R_3$ and $R_4$ form an annulated aromatic ring, or when the atom to which it would be attached is nitrogen, is absent;

$R_5$ and $R_6$ is each independently H, $C_{1-6}$ alkyl, hydroxy$C_{1-6}$ alkyl, amino$C_{1-6}$ alkyl, phenyl$C_{1-6}$ alkyl, carboxy$C_{1-6}$ alkyl, $C_{1-6}$ alkenyl, (phenyl$C_{1-3}$ alkoxy)$C_{1-3}$ alkyl, ($C_{1-6}$ acyloxy)$C_{1-6}$ alkyl, ($C_{1-6}$ alkoxycarbonyl)$C_{1-6}$ alkyl, (mono- or di-$C_{1-6}$ alkyl) amino$C_{1-6}$ alkyl ($C_{1-6}$ alkyl)aminocarbonyl$C_{1-6}$ alkyl, ($C_{1-6}$ acylamino)$C_{1-6}$ alkyl, (amino$C_{1-3}$ alkylphenyl)$C_{1-3}$ alkyl, or aminodeoxysugar;

$R_7$ and $R_8$ is each independently H, amino, nitro, hydroxy, halogen, $C_{1-6}$ alkoxy, phenyl$C_{1-6}$ alkoxy or carboxy$C_{1-6}$ alkyl ester;

$R_9$ is H, $C_{1-6}$ alkyl, phenyl, halophenyl or phenyl$C_{1-6}$ alkyl and wherein when $R_5$ and $R_9$ together comprise 3–5 carbons they may be linked to generate a cyclic moiety which may be amino$C_{1-6}$ alkyl substituted;

and wherein at least one of $R_1$ to $R_9$ is not H and wherein when the only one of $R_1$ to $R_9$ which is not H is $R_9$, $R_9$ is not methyl;

and pharmaceutically acceptable salts thereof.

The compounds of formula (IA), in which at least one of $R_5$ and $R_6$ carries an amino, carboxy or hydroxy group; and pharmaceutically acceptable salts thereof, may be prepared by, a) deprotecting a compound of formula (II) corresponding to formula (IA) but in which at least one of $R_5$ and $R_6$ carries a protected amino, carboxy or hydroxy group, or b) converting a compound of formula (IA), in which at least one of $R_5$ and $R_6$ carries an amino or carboxy group
   i) to a pharmaceutically acceptable salt thereof, or vice versa; or
   ii) a pharmaceutically acceptable salt of a compound of formula (IA) into a different pharmaceutically acceptable salt.

The compounds of formula (IA), in which $R_6$ is hydrogen, may be prepared by reacting a compound of formula (I):

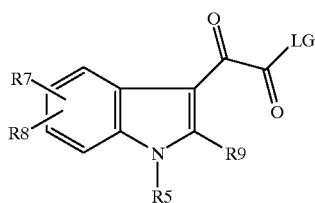

(III)

wherein $R_5$, $R_7$, $R_8$, and $R_9$ are as defined in formula (IA) and LG is a leaving group, e.g:

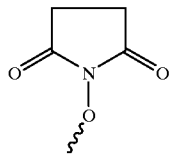

with a compound of formula (IV):

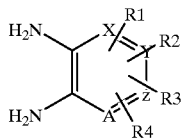

(IV)

wherein A, X, Y, and Z are as defined in formula (I), and $R_1$–$R_4$ are as defined in formula (IA), in a suitable solvent, e.g. THF, at about 10–30° C., e.g. for about 16 hours.

When $R_5$ in formula (III) carries an amino, carboxy or hydroxy group, these groups should be suitably protected. The protecting groups may be removed in a subsequent deprotecting step.

The compounds of formula (IA), when $R_6$ is other than H, may be prepared by reacting a compound of formula (II) which corresponds to formula (IA), but in which $R_6$ is H, with a suitable alkylating agent, e.g methyl iodide in the presence of a base, e.g. sodium hydride. The alkylating step may be carried out in a suitable solvent e.g dimethyl formamide at about 10–30° C. for e.g 2 hours.

When $R_5$ in formula (II) and/or the alkylating agent carries an amino, carboxy or hydroxy group, such groups should be suitably protected. The protecting groups may be removed in a subsequent deprotecting step.

The compounds of formula (II) may be prepared by (i) reacting a compound of formula (III), as defined above, with a compound of formula (IV), as defined above, in a suitable solvent e.g. THF, at about 10–30° C., e.g. for 16 h ,or (ii) by alkylating the product of (i) with a suitable alkylating agent when $R_5$ in formula (III) and/or the alkylating agent carries an amino, carboxy or hydroxy group, these should be in a protected form.

In all processes above, the protecting groups and conditions for deprotection are well known to those skilled in the art. Suitable protecting groups for amino groups are e.g phthaloyl groups and the deprotecting agent may be methylamine in e.g. water. The deprotecting step may be carried out in a suitable solvent, e.g tetrahydrofuran at about 10–30° C., e.g for about 5 hours. Suitable protecting groups for carboxy groups are e.g t-butyl groups and the deprotection step may be carried out in trifluoro acetic acid at about 10–30 ° C., e.g for about 4 hours. The hydroxy groups are protected as their corresponding acetoxy groups and the deprotecting agent may be methylamine in e.g. water. The deprotecting step may be carried out in a suitable solvent, e.g tetrahydrofuran at about 10–30° C., e.g for about 16 hours.

In process b) the conversion may be carried out by conventional processes, e.g.

i) reaction of the free base with an acid containing the desired anion, or by careful basification of the salt, or ii) reaction of the free acid with a base containing the desired cation, or by careful acidification of the salt.

The reaction may be carried out in a suitable solvent, e.g. methanol or methylene chloride.

Compounds of formula (I) which are not of formula (IA) may be made by analogous processes to those described above for compounds of formula (IA).

The starting materials for the above processes may be made by the methods set out in the Examples or by methods analogous thereto. Other conventional methods for making the starting materials will be evident to those skilled in the art.

The compounds of formula (I), and pharmaceutically acceptable salts thereof, are useful because they demonstrate pharmacological activity. In particular they demonstrate activity as kinase inhibitors, especially PKC inhibitors, e.g. as is shown by their activity in the in vitro assays described in Granet, R. A. et al, Analyt. Biochem. 1987; 163, 458–463; Olsson, H. et al, Cell Signal 1989, 1, 405–410; Chakravarthy, B. R. et al, Analyt. Biochem. 1991, 196, 144–150 and Bergstrand, H et al, J. Pharm. Exp. Ther. 1992; 263(3), 1334–1346.

In appropriate cellular systems, the compounds of formula (I) and pharmaceutical acceptable salts thereof, can also reduce the generation of inflammatory mediators. For example, the compounds can inhibit oxygen radical generation and generation of pro-inflammatory cytokines in monocytes. The compounds are especially useful as inhibitors of one or more cytokines selected from IL-1β, TNF-α, GM-CSF or IL-8.

The compounds of the invention are indicated for use in the treatment of inflammatory, immunological, bronchopulmonary, cardiovascular, oncological or CNS-degenerative disorders. Preferably for oral or topical treatment of inflammatory and/or immunological disorders, such as the oral or topical treatment of airway diseases involving inflammatory conditions, e.g. asthma, bronchitis or atopic diseases, e.g. rhinitis or atopic dermatitis; inflammatory bowel diseases, e.g. Crohn's disease or colitis; autoimmune diseases e.g. multiple sclerosis, diabetes, atherosclerosis, psoriasis, systemic lupus erythematosus or rheumatoid arthritis; malignant diseases, e.g. skin or lung cancer; HIV infections or AIDS; or for inhibiting rejection of organs/transplants.

The dose of the compound to be administered will depend upon the relevant indication, the age, weight and sex of the patient and may be determined by a physician. The dosage will preferably be in the range of from 0.1 mg/kg to 100 mg/kg.

The compounds may be administered topically, e.g. to the lung and/or the airways, in the form of solutions, suspensions, HFA areosols or dry powder formulations, e.g. formulations in the inhaler denice known as the Turbuhaler® ; or systemically, e.g. by oral administration in the form of tablets, pills, capsules, syrups, powders or granules, or by parenteral administration, e.g. in the form of sterile parenteral solutions or suspensions, or by rectal administration, e.g. in the form of suppositories.

The compounds of the invention may be administered on their own or as a pharmaceutical composition comprising the compound of the invention in combination with a pharmaceutically acceptable diluent, adjuvant or carrier. Particularly preferred are compositions not containing material capable of causing an adverse, e.g. an allergic, reaction.

Dry powder formulations and pressurized HFA aerosols of the compounds of the invention may be administred by oral or nasal inhalation. For inhalation the compound is desireably finely divided. The finely divided compound preferably has a mass median diameter of less than 10 μm, and may be suspended in a propellant mixture with the assistance of a dispersant, such as a $C_8$–$C_{20}$ fatty acid or salt thereof, (e.g. oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound with a carrier substance, e.g. a mono-, di- or polysaccharide, a sugar alcohol, or an other polyol. Suitable carriers are sugars, e.g. lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system the active compound, with or without a carrier substance, is delivered to the patient.

For oral administration the active compound may be admixed with an adjuvant or a carrier, e.g. lactose, saccharose, sorbitol, mannitol; a starch, e.g. potato starch, corn starch or amylopectin; a cellulose derivative; a binder, e.g. gelatine orpolyvinylpyrrolidone, and/or a lubricant, e.g. magnesium stearate, calcium stearate, polyethylene glycol, a wax, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet may be coated with a suitable polymer dissolved in a readily volatile organic solvent.

For the preparation of soft gelatine capsules, the compound may be admixed with e.g. a vegetable oil or polyethylene glycol. Hard gelatine capsules may contain granules of the compound using either the above mentioned excipients for tablets. Also liquid or semisolid formulations of the drug may be filled into hard gelatine capsules. Liquid preparations for oral application may be in the form of syrups or suspensions, for example solutions containing the compound, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention may also be administered in conjunction with other compounds used for the treatment of the above conditions.

The term 'medical therapy' as used herein is intended to include prophylactic, diagnostic and therapeutic regimens carried out in vivo or ex vivo on humans or other mammals.

Compounds of the present invention include all stereoisomers, pure and mixed racemates, and mixtures thereof.

In compounds of formula (IA) of the present invention, the following independent preferences apply:

$R_5$ and/or $R_6$ carries a hydroxy or amino group, at least one of Y and Z are substituted, position 5 of the indole is substituted, at least one of Y and Z are substituted with halo, methoxy or carboxylic ester, $R_9$ is H or alkyl and is most preferably H, when $R_5$ or $R_6$ is an aminodeoxysugar, it is preferably a six membered ring, when $R_5$ and $R_9$ together form a cyclic moiety, it is preferably a six membered ring, three or four of X,Y,Z and A are carbon, and/or $R_1$ and $R_2$, $R_2$ and $R_3$, or $R_3$ and $R_4$, and most preferably $R_2$ and $R_3$, form an annulated aromatic ring.

The most preferred compounds of the present invention are as follows:

3-[3-(4-Methyl-3-oxo-3,4-dihydro-quinoxalin-2-yl)-indol-1-yl]-propyl-ammonium acetate, 3-[3-(6,7-Dichloro-3-oxo-3,4-dihydro-quinoxalin-2-yl)-indol-1-yl]-propyl-ammonium acetate, 3-[3-(6,7-Dichloro-3-oxo-3,4-dihydro-quinoxalin-2-yl)-5-methoxycarbonyl-indol-1-yl]-propyl-ammonium acetate, 3-[3-(6,7-Dichloro-4-methyl-3-oxo-3,4-dihydro-quinoxalin-2-yl)-5-methoxycarbonyl-indol-1-yl]-propyl-ammonium acetate, 3-[5-Methoxycarbonyl-3-(7-methoxy-3-oxo-3,4-dihydro-quinoxalin-2-yl)-indol-1-yl]-propyl-ammonium acetate, 3-[3-(4-tert-Butoxycarbonylmethyl-7-methoxy-3-oxo-3,4-dihydro-quinoxalin-2-yl)-5-methoxycarbonyl-indol-1-yl]-propyl-ammonium acetate, 3-[3-(4-(3-Ammoniumpropyl)-3-oxo-3,4-dihydro-quinoxalin-2-yl)-indol-1-yl]-propyl-ammonium bis trifluoroacetate, Dimethyl-{3-[3-(1-methyl-1H-indol-3-yl)-2-oxo-2H-quinoxalin-1-yl]-propyl}-ammonium trifluoroacetate, 3-[3-(3-Oxo-3,4-dihydro-benzo[g]quinoxalin-2-yl)-indol-1-yl]-propyl-ammonium acetate, 3-[6-Benzyloxy-3-(7-methoxy-4-methy-3-oxo-3,4-dihydro-quinoxalin-2-yl)-indol- 1-yl]-propyl-ammonium acetate, 3-[5-Benzyloxy-3-(4-tert-butoxycarbonylmethyl-7-methoxy-3-oxo-3,4-dihydro-quinoxalin-2-yl)-indol-1-yl]-propyl-ammonium acetate, 3-[2-(4-Chloro-phenyl)-3-(7-methoxy-3-oxo-3,4-dihydro-quinoxalin-2-yl)-indol-1-yl]-propyl-ammonium acetate, 3-[2-(4-Chloro-phenyl)-3-(7-methoxy-4-methyl-3-oxo-3,4-dihydro-quinoxalin-2-yl)-indol-1-yl]-propyl-ammonium acetate, 3-[3-(6,7-Dichloro-4-methyl-3-oxo-3,4-dihydro-quinoxalin-2-yl)-2-ethyl-indol-1-yl]-propyl-ammonium acetate, 3-[3-(5-Methyl-3-oxo-3,4-dihydro-quinoxalin-2-yl)-6-nitro-indol-1-yl]-propyl-ammonium acetate, 3-[6-Nitro-3-(6-nitro-3-oxo-3,4-dihydro-quinoxalin-2-yl)-indol-1-yl]-propyl-ammonium acetate, 4-[3-(3-Oxo-3,4-dihydro-quinoxalin-2-yl)-indol-1-ylmethyl]benzyl-ammonium acetate, 3-[3-(4-Methyl-3-oxo-3,4-dihydro-quinoxalin-2-yl)-indol-1-ylmethyl]benzyl-ammonium trifluoroacetate, 3-[3-(4-Benzyl-3-oxo-3,4-dihydro-quinoxalin-2-yl)-indol-1-yl]-propyl-ammonium trifluoroacetate;

and the corresponding free amines thereof and other pharmaceutically acceptable salts thereof.

The most preferred compound of the present invention is:
3-[3-(3-Oxo-3,4-dihydro-benzo[g]quinoxalin-2-yl)-indol-1-yl]-propyl-ammonium acetate,
and the corresponding free amines thereof and other pharmaceutically acceptable salts thereof.

The following Examples illustrate, but in no way limit the invention.

All reactions were performed in dried glassware under Ar or $N_2$ unless otherwise noted. Tetrahydrofuran was distilled from sodium/benzophenone. Dimethyl formamide was distilled from calcium hydride, or dried over molecular sieves. Other solvents and all commercial reagents were used as received.

$^1$H-NMR spectra were recorded on a Varian XL-300 or Unity-500+instrument. The central solvent peaks of chloroform-d ($\delta_H$ 7.24 ppm), methanol-$d_4$ ($\delta_H$ 3.34 ppm) and dimethyl sulphoxide-$d_6$ ($\delta_H$ 2.50 ppm) were used as internal references. Low-resolution mass spectra and accurate mass determinations were recorded on an Autospec-Q, Fisons Analytical, double focusing sector instrument equiped with a LSIMS interface.

EXAMPLE 1

{1-[3-(1,3-Dioxo-1,3-dihydroisoindol-2-yl)-propyl]-1H-indol-3-yl}-oxoacetic acid 2,5-dioxopyrrolidin-1-yl ester) [intermediate]

1-[3-(1, 3-Dioxo-1,3-dihydroisoindol-2-yl)-propyl]-1H-indol (1.00 g, 3.29 mmol) was dissolved in dichloromethane (10 ml) and cooled to 0° C. Oxalylchloride (0.28 ml, 3.29 mmol) was added and the reaction kept at 0° C. for 30 minutes before the addition of N-hydroxysuccinimide (0.38 g, 3.29 mmol) followed by careful addition of pyridine (0.53 ml, 6.57 mmol).

After stirring the reaction for 1 hour at room temperature brine (5%, 10 ml) was added and the phases separated, the organic phase was washed with brine (5%, 2×10 ml), dried over $Na_2SO_4$ followed by removal of the solvent in vacuo. Crystallisation of the crude product from ethyl acetate—hexane yields the title product, 1.06 g (69%).

$^1$H-NMR (500 MHz, $CDCl_3$): δ 2.36 (2H, p, J 6.9 Hz), 2.93 (4H, s), 3.82 (2H, t, J 6.5 Hz), 4.29 (2H, t, J 7.5 Hz), 7.33–7.44 (3H, m), 7.70–7.75 (2H, m), 7.78–7.83 (2H, m), 8.32–8.36 (1H, m), 8.50 (1H, s).

FAB-MS: m/z 474 [MH+]

EXAMPLE 2

A) 3-[3-(3-Oxo-3 ,4-dihydro-quinoxalin-2-yl)-indol-1-yl]-propyl-ammonium acetate 1,2-Phenylenediamine (0.021 g, 0.20 mmol) and the product of Example 1 (0.075 g, 0.16 mmol) was dissolved in tetrahydrofuran (1 ml). Stirring overnight yields 2-(3-(3-(3-oxo-3,4-dihydroquinoxalin-2-yl)-inol-1-yl)propyl)-isoindol-1,3-dione as a yellow precipitate that was filtered off and washed with tetrahydrofuran.

$^1$H-NMR (500, MHz, DMSO-d6): δ 2.18 (2H, p, J 7.1 Hz), 3.71 (2H, t, J 6.6 Hz), 4.44 (2H, t, J 7.4 Hz), 7.26–7.36 (4H, m), 7.45 (1H, t, J 7.4 Hz), 7.67 (1H, d, J 8.3 Hz), 7.81–7.85 (2H, m), 7.85–7.89 (3H, m), 8,91 (1H, d, J 7.5 Hz), 9.03 (1H, s), 12.44 (1H, s, NH).

FAB-MS: m/z 449.3 [MH+]

The precipitate was suspended in tetrahydrofuran (1 ml) and aqueous methylamine (40%, 0.7 ml) was added. After stirring for 5 hours the solvent was removed in vacuo. 3-(1-(3-Aminopropyl)-1H-indol-3-yl)-1H-quinoxalin-2-one was crystallised from water and treated with aqueous acetic acid (1 M, 1 ml) to obtain the title compound as a yellow solid, 0.045 g (75%), after freeze drying.

$^1$H-NMR (500 MHz, $CD_3OD$): δ 1.92 (3H, s), 2.26 (2H, dt, J 15.7, 7.0 Hz), 2.92–2.98 (2H, m), 4.43 (2H, t, J 6.9 Hz), 7.28–7.40 (4H, m), 7.46 (1H, t, J 7.5 Hz), 7.56 (1H, d, J 7.5 Hz), 7.92 (1H, d, J 8.0 Hz), 8.87 (1H, s), 8.96 (1H, d, J 7.6 Hz).

FAB-MS: m/z 319.1 [MH+]

B) 3-[3-(6-Fluoro-3-oxo-3,4-dihydro-quinoxalin-2-yl)-indol-1-yl]propyl-ammonium acetate The title compound was prepared in 89% yield as described in A) starting from 4-fluoro-1,2-phenylenedi amine.

$^1$H-NMR (500 MHz, DMSO-$d_6$): δ 1.83 (3H, s), 1.99 (2H, p, J 7.1 Hz), 2.67 (2H, t, J 7.0 Hz), 4.42 (2H, t, J 7.0 Hz), 7.27–7.37 (4H, mn), 7.67 (1H, d, J 7.6 Hz), 7.70 (1H, d, J 9.5 Hz), 8.91 (1H, d, J 7.9 Hz), 9.04 (1H, s).

FAB-MS: rn/z 337.1 [MH+]

C) 3-[3-(7-Methoxy-3-oxo-3,4-dihydro-quinoxalin-2-yl)-indol-1-yl]propyl-ammonium acetate The title compound was prepared in 83% yield as described in A) starting from 4-methoxy-1,2-phenylenediamine.

$^1$H-NMR (500 MHz, $CD_3OD$): δ 1.95 (3H, s), 2.29 (2H, dt, J 15.2, 6.8 Hz), 2.96–3.00 (2H, m), 3.96 (3H, s), 4.45 (2H, t, J 6.8 Hz), 7.13 (1 H, dd, J 78.9, 2.6 Hz), 7.27 (1H, d, J 89.2 Hz), 7.32–7.39 (2H, m), 7.44 (1H, d, J 2.6 Hz), 7.59 (.H, d, J 7.9 Hz), 8.89 (1H, s), 8.99 (1H, d, J 7.5 Hz).

FAB-MS: m/z 349.1 [MH+]

D) 3-[3-(2-Oxo-1,2-dihydro-pyrido[2,3-b]pyrazin-3-yl)-indol-1-yl]propyl-ammonium acetate The title compound was prepared in 85% yield as described in A) starting from 24-diaminopyridine.

$^1$H-NMR (500 MHz, $CD_3OD$): δ 1.95 (3H, s), 2.30 (2H, dt, J 15.6,7.1 Hz), 2.98–3.03 (2H, m), 4.47 (2H, t, J 7.0 Hz), 7.36–7.4 1 (2H, m), 7.58–7.62 (J H, m), 8.72 (1H, s), 8.96 (1H, s), 9.06–9.10 (1H, m), 9.18 (1H, s).

FAB-MS: m/z 320.1 [MH+]

E) 3-[3-(4-Hydroxy-6-oxo-5,6-dihydro-pteridin-7-yl)-indol-1-yl]propyl-ammonium acetate The title compound was prepared in 38% yield as described in A) starting from 5,6-diamino-4-hydroxypyrimidine.

$^1$H-NMR (500 MHz, DMSO-$d_6$/$D_2O$): δ 1.89 (3H, s), 2.08 (2H, p, J 7.0 Hz), 2.80 (2H, t, J 7.1 Hz), 4.45 (2H, t, J 7.1 Hz), 7.26–7.33 (2H, m), 7.66 (1H, d, J 8.1 Hz), 8.00 (1H, s), 8.91 (1H, d, J 7.5 Hz), 9.20 (1H, s).

FAB-MS: m/z 337.0 [M+]

F) 3-[3-(6-Oxo-5,6-dihydro-pteridin-7-yl)-indol-1-yl]-propyl-ammonium acetate

The title compound was prepared in 38% yield as described in A) starting from 5,6-diaminopyrimidine.

FAB-MS: m/z 320.2 [M+]

G) 3-[3-(5-Hydroxy-3-oxo-3,4-dihydro-quinoxalin-2-yl)-indol-1-yl]propyl-ammonium acetate The title compound was prepared in 22% yield as described in A) starting from 2,3-diaminophenol.

FAB-MS: m/z 335.1 [MH+]

H) 3-[3-(3-Oxo-3,4-dihydro-pyrido[3,4-b]pyrazin-2-yl)-indol-1-yl]-propyl-ammonium acetate The title compound was prepared in 38% yield as described in A) starting from 3,4-diaminopyridine.

FAB-MS: m/z 320.2 [MH+]

I) 3-[3-(8-Nitro-3-oxo-3,4-dihydro-quinoxalin-2-yl)-indol-1-yl]-propyl-ammonium acetate The title compound was prepared in 79% yield as described in A) starting from 3-nitro-1,2-phenylenediamine.
FAB-MS: m/z 364.1 [MH+]

J) 3-[3-(6-Nitro-3-oxo-3,4-dihydro-quinoxalin-2-yl)-indol-1-yl]-propyl-ammonium acetate
The title compound was prepared in 55% yield as described in A) starting from 4-nitro-1,2-phenylenediamine.
FAB-MS: m/z 364.1 [MH+]

K) 3-[3-(6,7-Dichloro-3-oxo-3,4-dihydro-quinoxalin-2-yl)-indol-1-yl]-propyl-ammonium acetate
The title compound was prepared in 93% yield as described in A) starting from 4,5-dichloro-1,2-phenylenediamine.
FAB-MS: m/z 387.0 [MH+]

L) 3-[3-(7-Methyl-3-oxo-3,4-dihydro-quinoxalin-2-yl)-indol-1-yl]-propyl-ammonium acetate
The title compound was prepared in 93% yield as described in A) starting from 4-methyl-1,2-phenylenediamine.
FAB-MS: m/z 333.2 [MH+]

M) 3-[3-(5-Methyl-3-oxo-3,4-dihydro-quinoxalin-2-yl)-indol-1-yl]-propyl-ammonium acetate
The title compound was prepared in 87% yield as described in A) starting from 3-methyl-1,2-phenylenediamine.
FAB-MS: m/z 333.2 [MH+]

N) 3-[3-(6,7-Dimethyl-3-oxo-3,4-dihydro-quinoxalin-2-yl)-indol-1-yl]-propyl-ammonium acetate
The title compound was prepared in 89% yield as described in A) starting from 4,5-dimethyl-1,2-phenylenediamine.
FAB-MS: m/z 347.2 [MH+]

O) 3-[3-(6-Methoxycarbonyl-3-oxo-3,4-dihydro-quinoxalin-2-yl)-indol-1-yl]-propyl-ammonium acetate
The title compound was prepared in 43% yield as described in A) starting from methyl 3,4-diaminobensoate.
FAB-MS: m/z 377.1 [MH+]

P) 3-[3-(6-Ethoxycarbonyl-3-oxo-3,4-dihydro-quinoxalin-2-yl)-indol-1-yl]propyl-ammonium acetate
The title compound was prepared in 78% yield as described in A) starting from ethyl 3,4-diaminobensoate.
FAB-MS: m/z 391.0 [MH+]

Q) 3-[3-(3-Oxo-6-trifluoromethyl-3,4-dihydro-quinoxalin-2-yl)-indol-1-yl]-propyl-ammonium acetate
The title compound was prepared in 85% yield as described in A) starting from 4-trifluoromethyl-1,2-phenylenediamine.
FAB-MS: m/z 387.1 [MH+]

EXAMPLE 3

3-[3-(4-Methyl-3-oxo-3,4-dihydro-quinoxalin-2-yl)-indol-1-yl]-propyl-ammonium Acetate A dispersion of sodium hydride, 55–60% in oil, (0.0075 g, 0.17 mmol) in dry dimethyl formamide (2 ml) was cooled to −20° C. A solution 2-{3-[3-(3-oxo-3,4-dihydro-quinoxalin-2-yl)-indol-1-yl]-propyl}-isoindol-1,3-dione (0.050 g, 0.11 mmol) in dry dimethyl formamide (2 ml), was added dropwise and the resulting mixture kept at −20° C. for 5 min and then at room temperature for another 15 min. The reaction mixture was cooled to −20° C and methyl iodide (0.017 g, 0.12 mmol, 7.7 μl) was added via a syringe. The resulting solution was allowed to reach room temperature whereupon 12 ml of diethyl ether was added. After 2 h at room temperature, 2-{3-[3-(4-methyl-3-oxo-3,4-dihydro-quinoxalin-2-yl)-indol-1-yl]-propyl}-isoindole-1,3-dione was precipitated.

The precipitate was collected by centrifugation, and then suspended in tetrahydrofuran (2 ml). Aqueous methylamine (1 ml) was added giving a homogenous light yellow solution. After stirring for 5 h, the free amine was precipitated. The solvent was evaporated and the precipitate suspended in 4 ml of water and then collected by centrifugation. The precipitate was treated with aqueous acetic acid (1 M, 1 ml) and freeze dried to give 0.019g (43%) of the title compound as a yellow solid.

$^1$H-NMR (400 MHz, CD$_3$OD): δ 1.95 (3H, s), 2.28 (2H, quintet, J 7.0 Hz), 2.97 (2H, bs), 3.85 (3H, s), 4.46 (2H, t, J 7.0 Hz), 7.30–7.40 (2H, m), 7.46 (1H, ddd, J 8.0, 7.2, 2.4 Hz), 7.56–7.62 (3H, m), 7.98 (1H, d, J 7.7 Hz), 8.90 (1H, s), 8.99 (1H, d, J 7.3 Hz).
FAB-MS: m/z 333.0 [MH+]

EXAMPLE 4

3-{1-(6-Amino-2,4,6-trideoxy-β-D-threo-hexopyranosyl)-1H-indol-3-yl}-1H-quinoxazolin-2-one trifluoro acetic acid salt a) 3-{1-(3-O-Benzoyl-6-phthalimido-2,4,6-trideoxy-β-D-threo-hexopyranosyl)-1H-indol-3-yl}-1H-quinoxalin-2-one 1(3-O-Benzoyl-6-phthalimido-2,4,6-trideoxy-β-D-threo-hexopyranosyl)-1H-indole (0.30 g, 0.62 mmol) was dissolved in dichloromethane (3 ml) and cooled to 0° C. Oxalyichloride (65 μl, 0.74 mmol) was added and the reaction mixture kept at 0° C. for 15 ml and then stirred at room temperature for another 45 minutes. N-hydroxysuccinimid (0.08 g 0.70 mmol) was added followed by careful addition of pyridine (0.10 ml, 1.23 mmol). The reaction mixture was stirred at room temperature for 16 hours and then washed twice with water. The organic layer was evaporated and the crude mixed with tetrahydrofuran (10 ml) and 1,2-diphenylenediamine (0.09 g, 0.80 mmol) and stirred at room temperature for 16 hours. The resulting percipitate was collected by centrifugation, washed twice with ether and dried to give 0.12 g (32%) of the subtitle product.

$^1$H-NMR (400 Mhz, DMSO-d$_6$): δ 1.63–1.74 (1H, m), 2.31–2.40 (2H, m), 2.55–2.62 (1H, m), 3.76 (H, dd, J 14.2, 5.4 Hz), 3.86 (1H, dd, J 14.0, 7.3 Hz), 4.29–4.3 8 (HH , m), 5.41–5.53 (1H, m), 6.08 (1H, dd, J 11.0, 1.9 Hz), 7.00 (1H, t, J 7.5 Hz), 7.22 (1H, t, J 7.5 Hz), 7.29–7.37 (2H, m), 7.45 (1H, d, J 7.5 Hz), 7.49 (1H, d, J 7. 9 Hz), 7.52–7.5 9 (2H, m), 7.69 (1H, t, J 7.5 Hz), 7.85 (4H, bs), 7.88 (1H, d, J 8.1 Hz), 8.01–8.06 (2H, m), 8.86 (1H, d, J 8.1 Hz), 9.05 (1H, s), 12.49 (1H, s).

b) The product from step a) (52.0 mg, 0.08 mmol) was dispersed in 2 ml of tetrahydrofuran. Aqueous methylamine was added (1 ml) and the mixture stirred at room temperature for 17 hours, The reaction mixture was eveporated and the crude filtered through a short column of silica gel using CH$_2$Cl$_2$/MeOH/NH$_3$ (100/10/1) as eluent. The solvents were evaporated and the crude amine subjected to reverse-phase column chromatography using a pre-packed column (Merck Lobaar, LiChroprep RP-8) and MeOHH$_2$O/TFA (70/30/0.1) as the eluent. The fractions co ntaining the product were partly evaporated and freeze dried to give 0.01 g (24%) of the title product.

$^1$H-NMR (500 Mhz, DMSO-d$_6$): δ 1.27–1.37 (1H, m), 1.95–2.05 (2H, m), 2.29–2.37 (1H, m), 2.88–3.00 (1H, m), 3.04–3.13 (1H , m), 3.93–4.08 (2H, m), 5.23 (8H, bs), 5.91 (mH, dd, J 11.2, 1.8 Hz), 7.29–7.36 (4H, m), 7.46 ((H , t, J 7.4 Hz), 7.75 ((H , t, J 7.9 Hz), 7.79 (2H, bs), 7.89 (1H, d, J 8.0 Hz), 8.89–8.93 (1H, m), 9.09 (1H, s), 12.51 (1H, s).
FAB-MS: m/z 391 [MH+]

EXAMPLE 5

3-[3-(4-(3-Ammoniumpropyl)-3-oxo-3,4-dihydro-quinoxalin-2-yl)-indol-1-yl]-propyl-ammonium Bis Trifluoroacetate A mixture of sodium hydride, 55–60% in oil, (0.029 g, 0.67 mmol) and 2-{3-[3-(3-oxo-3,4-dihydro-quinoxalin-2-yl)-indol-1yl]-propyl}-isoindol-1,3-dione (0.25 g, 0.56 mmol) in dry dimethyl formamide (4 ml) was stirred at −20° C. for 10 min and then at room temperature for another 30 min. A solution of 2-(3-Bromopropyl)-isoindole-1,3-dione (0.20 g 0.75 mmol) in 2 ml dimethyl formamide was added and the rection mixture stirred at room temperature for 30 min and then at 60° C. for 3 hours. The percipitate formed was separated by centrifugation, washed with ethyl acetate and dried. The crude percipitate was suspended in tetrahydrofuran (5 ml) and aqeuous methylamine (3 ml) and stirred at room temperature for 3.5 hours. The solvent was evaporated and the residue washed with 10 ml of water. The crude mixture was subjected to reverse-phase column chromatography using a pre-packed column (Merck Lobar, LiChroprep RP-8) and MeOH/H$_2$O/TFA (70/30/0.1) as the eluent. The fractions containing the product were partly evaporated and freeze dried to give 0.02g (6%) of the title product.

$^1$H-NMR (500 Mhz, CD$_3$OD): δ 2.29 (2H, quintet, J 7.6 Hz), 2.39 (2H, quintet, J 7.1 Hz), 2.99 (2H, t, J 7.8 Hz), 3.20 (2H, t, J 7.3 Hz), 4.50 (2H, t, J 7.1 Hz), 4.84–4.89 (2H, triplett hidden under the solvent), 7.31 (1H, td, J 7.6 1.0 Hz), 7.36 (1H, td, J 7.8 1.2 Hz), 7.56–7.66 (3H, m), 7.78–7.84 (1H, m), 8.04–8.09 (1H, m), 8.36 (1H, s), 8.94 (1H, d, J 7.9 Hz).

FAB-MS: m/z 376 [MH+]

The following examples were prepared following the methods described above in Examples 1 to 4. Removal of protecting groups were performed according to standard literature methods.

EXAMPLE 6

3-[3-(4-tert-Butoxycarbonylmethyl-3-oxo-3,4-dihydro-quinoxalin-2-yl)-2-methyl-indol-1-yl]-propyl-ammonium acetate
FAB-MS: m/z 447 [MH+]

EXAMPLE 7

3-[5-Benzyloxy-3-(4-methyl-3-oxo-3,4-dihydro-quinoxalin-2-yl)-indol-1-yl]-propyl-ammonium acetate
FAB-MS: m/z 439 [MH+]

EXAMPLE 8

3-[3-(4-Methyl-3-oxo-3,4-dihydro-quinoxalin-2-yl)-6-nitro-indol-1-yl]propyl-ammonium acetate
FAB-MS: m/z 378 [MH+]

EXAMPLE 9

3-[3-(4-tert-Butoxycarbonylmethyl-3-oxo-3,4-dihydro-quinoxalin-2-yl)-2-(4-chloro-phenyl)-indol-1-yl]-propyl-ammonium acetate
FAB-MS: m/z 544 [MH+]

EXAMPLE 10

3-[2-Ethyl-3-(4-methyl-3-oxo-3,4-dihydro-quinoxalin-2-yl)-indol-1-yl]propyl-ammonium acetate
FAB-MS: m/z 361 [MH+]

EXAMPLE 11

3-[6-Benzyloxy-3-(4-tert-butoxycarbonylmethyl-3-oxo-3,4-dihydro-quinoxalin-2-yl)-indol-1-yl]-propyl-ammonium acetate
FAB-MS: m/z 539 [MH+]

EXAMPLE 12

3-[5-Methoxycarbonyl-3-(4-methyl-3-oxo-3,4-dihydro-quinoxalin-2-yl)-indol-1-yl]propyl-ammonium acetate
FAB-MS: m/z 391 [MH+]

EXAMPLE 13

3-[3-(4,7-Dimethyl-3-oxo-3,4-dihydro-quinoxalin-2-yl)-2-methyl-indol-1-yl]propyl-ammonium acetate
FAB-MS: ni/z 361 [MH+]

EXAMPLE 14

3-[5-Benzyloxy-3-(4-tert-butoxycarbonylmethyl-7-methyl-3-oxo-3 ,4-dihydro-quinoxalin-2-yl)-indol-1-yl]-propyl-ammonium acetate
FAB-MS: m/z 553 [MH+]

EXAMPLE 15

3-[3-(4-tert-Butoxycarbonylmethyl-7-methyl-3-oxo-3,4-dihydro-quinoxalin-2-yl)-6-nitro-indol-1-yl]-propyl-ammonium acetate
FAB-MS: m/z 492 [MH+]

EXAMPLE 16

3-[2-(4-Chloro-phenyl)-3-(4,7-dimethyl-3-oxo-3,4-dihydro-quinoxalin-2-yl)-indol-1-yl]-propyl-ammonium acetate
FAB-MS: m/z 457 [MH+]

EXAMPLE 17

3-[3-(4-tert-Butoxycarbonylmethyl-7-methyl-3-oxo-3,4-dihydro-quinoxalin-2-yl)-2-ethyl-indol-1-yl]-propyl-ammonium acetate
FAB-MS: m/z 475 [MH+]

EXAMPLE 18

3-[6-Benzyloxy-3-(4,7-dimethyl-3-oxo-3,4-dihydro-quinoxalin-2-yl)-indol-1-yl]propyl-ammonium acetate
453 [MH+]

EXAMPLE 19

3-[3-(4-tert-Butoxycarbonylmethyl-7-methyl-3-oxo-3 ,4-dihydro-quinoxalin-2-yl)-5-methoxycarbonyl-indol-1-yl]-propyl-ammonium acetate
505 [MH+]

EXAMPLE 20

3-[3-(4-tert-Butoxycarbonylmethyl-6,7-dichloro-3-oxo-3,4-dihydro-quinoxalin-2-yl)-2-methyl-indol-1-yl]-propyl-ammonium acetate
516 [MH+]

EXAMPLE 21

3-[5-Benzyloxy-3-(6,7-dichloro-4-methyl-3-oxo-3,4-dihydro-quinoxalin-2-yl)-indol-1-y1]-propyl-ammonium acetate
508 [MH+]

EXAMPLE 22

3-[3-(6,7-Dichloro-4-methyl-3-oxo-3,4-dihydro-quinoxalin-2-yl)-2-ethyl-indol-1-yl]-propyl-ammonium acetate
FAB-MS: m/z 430 [MH+]

EXAMPLE 23

3-[3-(6,7-Dichloro-4-methyl-3-oxo-3,4-dihydro-quinoxalin-2-yl)-5-methoxycarbonyl-indol-1-yl]-propyl-ammonium acetate
FAB-MS: m/z 460 [MH+]

EXAMPLE 24

3-[5-Benzyloxy-3-(4-tert-butoxycarbonylmethyl-6-nitro-3-oxo-3,4-dihydro-quinoxalin-2-yl)-indol-1-yl]-propyl-ammonium acetate
FAB-MS: m/z 584 [MH+]

EXAMPLE 25

3-[3-(4-tert-Butoxycarbonylmethyl-6-nitro-3-oxo-3,4-dihydro-quinoxalin-2-yl)-6-nitro-indol-1-yl]-propyl-ammonium acetate
FAB-MS: m/z 523 [MH+]

EXAMPLE 26

3-[3-(4-tert-Butoxycarbonylmethyl-6-nitro-3-oxo-3,4-dihydro-quinoxalin-2-y1)-5-methoxycarbonyl-indol-1-yl]-propyl-ammonium acetate
FAB-MS: m/z 536 [MH+]

EXAMPLE 27

3-[5-Benzyloxy-3-(4,5-dimethyl-3-oxo-3,4-dihydro-quinoxalin-2-yl)-indol-1-yl]-propyl-ammonium acetate
FAB-MS: m/z 453 [MH+]

EXAMPLE 28

3-[3-(4,5-Dimethyl-3-oxo-3,4-dihydro-quinoxalin-2-yl)-6-nitro-indol-1-yl]propyl-ammonium acetate
FAB-MS: m/z 392 [MH+]

EXAMPLE 29

3-[3-(4-tert-Butoxycarbonylmethyl-5-methyl-3-oxo-3,4-dihydro-quinoxalin-2-yl)-2-(4-chloro-phenyl)-indol-1-yl]-propyl-ammonium acetate
FAB-MS: m/z 558 [MH+]

EXAMPLE 30

3-[5-Benzyloxy-3-(4-tert-butoxycarbonylmethyl-7-methoxy-3-oxo-3 ,4-dihydro-quinoxalin-2-yl)-indol-1-yl]-propyl-ammonium acetate
FAB-MS: m/z 569 [MH+]

EXAMPLE 31

3-[3-(4-tert-Butoxycarbonylmethyl-7-methoxy-3-oxo-3,4-dihydro-quinoxalin-2-yl)-6-nitro-indol-1-yl]-propyl-ammonium acetate
FAB-MS: m/z 508 [MH+]

EXAMPLE 32

3-[2-(4-Chloro-phenyl)-3-(7-methoxy-4-methyl-3-oxo-3,4-dihydro-quinoxalin-2-yl)-indol-1-yl]-propyl-ammonium acetate
FAB-MS: m/z 473 [MH+]

EXAMPLE 33

3-[3-(4-tert-Butoxycarbonylmethyl-7-methoxy-3-oxo-3,4-dihydro-quinoxalin-2-yl)-2-ethyl-indol-1-yl]-propyl-ammonium acetate
FAB-MS: mlz 491 [MH+]

EXAMPLE 34

3-[6-Benzyloxy-3-(7-methoxy-4-methyl-3-oxo-3,4-dihydro-quinoxalin-2-yl)-indol-1-yl]-propyl-ammonium acetate
FAB-MS: m/z 469 [MH+]

EXAMPLE 35

3-[3-(4-tert-Butoxycarbonylmethyl-7-methoxy-3-oxo-3,4-dihydro-quinoxalin-2-yl)-5-methoxycarbonyl-indol-1-yl]-propyl-ammonium acetate
FAB-MS: m/z 521 [MH+]

EXAMPLE 36

3-[6-Hydroxy-3-(7-methoxy-4-methyl-3-oxo-3,4-dihydro-quinoxalin-2-yl)-indol-1-yl]-propyl-ammonium acetate
FAB-MS: m/z 379 [MH+]

EXAMPLE 37

5-[3-(1H-Indol-3-yl)-6,7-dimethyl-2-oxo-2H-quinoxalin-1-yl]pentyl-ammonium trifluoroacetate
FAB-MS: m/z 357 [MH+]

EXAMPLE 38

3-(1-Butyl-5-methoxy-1H-indol-3-yl)-1H-quinoxalin-2-one
FAB-MS: m/z 348 [MH+]

EXAMPLE 39

3-[5-Bromo-3-(3-oxo-3,4-dihydro-quinoxalin-2-yl)-indol-1-ylmethyl]benzyl-ammonium acetate
FAB-MS: m/z 459 [MH+]

EXAMPLE 40

Acetic acid 3-[3-(3-oxo-3,4-dihydro-quinoxalin-2-yl)-indol-1-yl]-propyl ester
FAB-MS: m/z 362 [MH+]

EXAMPLE 41

3-[3-(3-Oxo-3,4-dihydro-quinoxalin-2-yl)-2-phenyl-indol-1-yl]propyl-ammonium acetate
FAB-MS: m/z 395 [MH+]

EXAMPLE 42

10-(3-Oxo-3,4-dihydro-quinoxalin-2-yl)-6,7,8,9-tetrahydro-pyrido[1,2-a]indol-8-ylmethyl-ammonium acetate
FAB-MS: m/z 345 [MH+]

EXAMPLE 43

1-Methyl-3-(1-methyl-1H-indol-3-yl)-1H-quinoxalin-2-one
FAB-MS: mlz 290 [MH+]

EXAMPLE 44

N-{3-[3-(3-Oxo-3,4-dihydro-quinoxalin-2-yl)-indol-1-yl]-propyl}-acetamide
FAB-MS: m/z 361 [MH+]

EXAMPLE 45

3-[3-(4-Methyl-3-oxo-3,4-dihydro-quinoxalin-2-yl)-indol-1-yl]propyl-ammonium acetate
FAB-MS: m/z 333 [MH+]

EXAMPLE 46

3-[3-(4-Methyl-3-oxo-3,4-dihydro-quinoxalin-2-yl)-indol-1-yl]-propyl-ammonium trifluoroacetate
FAB-MS: m/z 333 [MH+]

EXAMPLE 47

3-(1-Benzyl-1H-indol-3-yl)-1H-quinoxalin-2-one
FAB-MS: m/z 352 [MH+]

EXAMPLE 48

4-[3-(3-Oxo-3,4-dihydro-quinoxalin-2-yl)-indol-1-yl]-butyl-ammonium acetate
FAB-MS: m/z 333 [MH+]

EXAMPLE 49

3-[3-(4-Benzyloxymethyl-3-oxo-3,4-dihydro-quinoxalin-2-yl)-indol-1-yl]-propyl-ammonium acetate
FAB-MS: m/z 439 [MH+]

EXAMPLE 50

3-[3-(4-Ethyl-3-oxo-3,4-dihydro-quinoxalin-2-yl)-indol-1-yl]-propyl-ammonium trifluoroacetate
FAB-MS: m/z 347 [MH+]

EXAMPLE 51

3-[3-(7-Benzyl-4-methyl-3-oxo-3,4-dihydro-quinoxalin-2-yl)-indol-1-yl]propyl-ammonium acetate
FAB-MS: m/z 423 [MH+]

EXAMPLE 52

3-[3-(4-Benzyl-3-oxo-3,4-dihydro-quinoxalin-2-yl)-indol-1-yl]propyl-ammonium trifluoroacetate
FAB-MS: m/z 409 [MH+]

EXAMPLE 53

3-[3-(4-Butyl-3-oxo-3,4-dihydro-quinoxalin-2-yl)-indol-1-yl]-propyl-ammonium trifluoroacetate
FAB-MS: m/z 375 [MH+]

EXAMPLE 54

3-[3-(4-Allyl-3-oxo-3,4-dihydro-quinoxalin-2-yl)-indol-1-yl]-propyl-ammonium trifluoroacetate
FAB-MS: m/z 359 [MH+]

EXAMPLE 55

3-[3-(4-Methylcarbamoylmethyl-3-oxo-3,4-dihydro-quinoxalin-2-yl)-indol-1-yl]propyl-ammonium trifluoroacetate
FAB-MS: m/z 390 [MH+]

EXAMPLE 56

3-[3-(4-tert-Butoxycarbonylmethyl-3-oxo-3,4-dihydro-quinoxalin-2-yl)-indol-1-yl]propyl-ammonium trifluoroacetate
FAB-MS: m/z 433 [MH+]

EXAMPLE 57

3-[3-(4-Carboxymethyl-3-oxo-3,4-dihydro-quinoxalin-2-yl)-indol-1-yl]propyl-ammonium trifluoroacetate
FAB-MS: m/z 377 [MH+]

EXAMPLE 58

3-(1-Methyl-1H-indol-3-yl)-1H-quinoxalin-2-one
FAB-MS: m/z 276 [MH+]

EXAMPLE 59

3-[3-(7-Benzyl-3-oxo-3,4-dihydro-quinoxalin-2-yl)-indol-1-yl]propyl-ammonium trifluoroacetate
FAB-MS: m/z 409 [MH+]

EXAMPLE 60

3-[3-(1-Methyl-1H-indol-3-yl)-2-oxo-2H-quinoxalin-1-yl]propyl-ammonium trifluoroacetate
FAB-MS: m/z 333 [MH+]

EXAMPLE 61

4-[3-(3-Oxo-3,4-dihydro-quinoxalin-2-yl)-indol-1-ylmethy]-benzyl-ammonium acetate
FAB-MS: m/z 381 [MH+]

EXAMPLE 62

2-[3-(3-Oxo-3,4-dihydro-quinoxalin-2-yl)-indol-1-yl]-ethyl-ammonium acetate
FAB-MS: m/z 305 [MH+]

EXAMPLE 63

3-[3-(3-Oxo-3,4-dihydro-quinoxalin-2-yl)-indol-1-ylmethyl]enzyl-ammonium acetate
FAB-MS: m/z 381 [MH+]

EXAMPLE 64

4-[3-(4-Methyl-3-oxo-3,4-dihydro-quinoxalin-2-yl)-indol-1-ylmethyl]-benzyl-ammonium trifluoroacetate
FAB-MS: m/z 395 [MH+]

EXAMPLE 65

3-[3-(4-Methyl-3-oxo-3,4-dihydro-quinoxalin-2-yl)-indol-1-ylmethyl]-benzyl-ammonium trifluoroacetate
FAB-MS: m/z 395 [MH+]

EXAMPLE 66

3-[2-Methyl-3-(3-oxo-3,4-dihydro-quinoxalin-2-yl)-indol-1-yl]-propyl-ammonium acetate
FAB-MS: m/z 333 [MH+]

EXAMPLE 67

3-[5-Benzyloxy-3-(3-oxo-3,4-dihydro-quinoxalin-2-yl)-indol-1-yl]-propyl-ammonium acetate
FAB-MS: m/z 425 [MH+]

EXAMPLE 68

3-[5-Amino-3-(3-oxo-3,4-dihydro-quinoxalin-2-yl)-indol-1-yl]-propyl-ammonium acetate
FAB-MS: m/z 334 [MH+]

EXAMPLE 69

3-[6-Nitro-3-(3-oxo-3,4-dihydro-quinoxalin-2-yl)-indol-1-yl]-propyl-ammonium acetate
FAB-MS: m/z 364 [MH+]

EXAMPLE 70

3-[2-(4-Chloro-phenyl)-3-(3-oxo-3,4-dihydro-quinoxalin-2-yl)-indol-1-yl]-propyl-ammonium acetate
FAB-MS: m/z 429 [MH+]

EXAMPLE 71

3-[2-Ethyl-3-(3-oxo-3,4-dihydro-quinoxalin-2-yl)-indol-1-yl]-propyl-ammonium acetate
FAB-MS: m/z 347 [MH+]

EXAMPLE 72

3-[6-Benzyloxy-3-(3-oxo-3,4-dihydro-quinoxalin-2-yl)-indol-1-yl]-propyl-ammonium acetate
FAB-MS: m/z 425 [MH+]

EXAMPLE 73

3-[5-Methoxycarbonyl-3-(3-oxo-3,4-dihydro-quinoxalin-2-yl)-indol-1-yl]-propyl-ammonium acetate
FAB-MS: m/z 377 [MH+]

EXAMPLE 74

3-[6-Hydroxy-3-(3-oxo-3,4-dihydro-quinoxalin-2-yl)-indol-1-yl]-propyl-ammonium acetate
FAB-MS: m/z 335 [MH+]

EXAMPLE 75

3-[2-Methyl-3-(7-methyl-3-oxo-3,4-dihydro-quinoxalin-2-yl)-indol-1-yl]propyl-ammonium acetate
FAB-MS: m/z 347 [MH+]

EXAMPLE 76

3-[5-Benzyloxy-3-(7-methyl-3-oxo-3,4-dihydro-quinoxalin-2-yl)-indol-1-yl]propyl-ammonium acetate
FAB-MS: rm/z 439 [MH+]

EXAMPLE 77

3-[5-Amino-3-(7-methyl-3-oxo-3,4-dihydro-quinoxalin-2-yl)-indol-1-yl]propyl-ammonium acetate
FAB-MS: m/z 348 [MH+]

EXAMPLE 78

3-[3-(7-Methyl-3-oxo-3,4-dihydro-quinoxalin-2-yl)-6-nitro-indol-1-yl]propyl-ammonium acetate
FAB-MS: m/z 378 [MH+]

EXAMPLE 79

3-[2-(4-Chloro-phenyl)-3-(7-methyl-3-oxo-3,4-dihydro-quinoxalin-2-yl)-indol-1-yl]-propyl-ammonium acetate
FAB-MS: m/z 444 [MH+]

EXAMPLE 80

3-[2-Ethyl-3-(7-methyl-3-oxo-3,4-dihydro-quinoxalin-2-yl)-indol-1-yl]propyl-ammonium acetate
FAB-MS: m/z 361 [MH+]

EXAMPLE 8

3-[6-Benzyloxy-3-(7-methyl-3-oxo-3,4-dihydro-quinoxalin-2-yl)-indol-1-yl]propyl-ammonium acetate
FAB-MS: m/z 439 [MH+]

EXAMPLE 82

3-[5-Methoxycarbonyl-3-(7-methyl-3-oxo-3,4-dihydro-quinoxalin-2-yl)-indol-1-yl]-propyl-ammonium acetate
FAB-MS: m/z 391 [MH+]

EXAMPLE 83

3-[6-Hydroxy-3-(7-methyl-3-oxo-3,4-dihydro-quinoxalin-2-yl)-indol-1-yl]-propyl-ammonium acetate
FAB-MS: m/z 349 [MH+]

EXAMPLE 84

3-[5-Benzyloxy-3-(6,7-dichloro-3-oxo-3,4-dihydro-quinoxalin-2-yl)-indol-1-yl]propyl-ammonium acetate
FAB-MS: m/z 494 [MH+]

EXAMPLE 85

3-[5-Amino-3-(6,7-dichloro-3-oxo-3,4-dihydro-quinoxalin-2-yl)-indol-1-yl]-propyl-ammonium acetate
FAB-MS: m/z 403 [MH+]

EXAMPLE 86

3-[3-(6,7-Dichloro-3-oxo-3,4-dihydro-quinoxalin-2-yl)-6-nitro-indol-1-yl]-propyl-ammonium acetate
FAB-MS: m/z 433 [MH+]

EXAMPLE 87

3-[2-(4-Chloro-phenyl)-3-(6,7-dichloro-3-oxo-3,4-dihydro-quinoxalin-2-yl)-indol-1-yl]-propyl-ammonium acetate
FAB-MS: m/z 498 [MH+]

EXAMPLE 88

3-[3-(6,7-Dichloro-3-oxo-3,4-dihydro-quinoxalin-2-yl)-2-ethyl-indol-1-yl]propyl-ammonium acetate
FAB-MS: m/z 416 [MH+]

EXAMPLE 89

3-[6-Benzyloxy-3-(6,7-dichloro-3-oxo-3,4-dihydro-quinoxalin-2-yl)-indol-1-yl]propyl-ammonium acetate
FAB-MS: m/z 494 [MH+]

EXAMPLE 90

3-[3-(6,7-Dichloro-3-oxo-3,4-dihydro-quinoxalin-2-yl)-5-methoxycarbonyl-indol-1-yl]-propyl-ammonium acetate
FAB-MS: m/z 446 [MH+]

EXAMPLE 91

3-[3-(6,7-Dichloro-3-oxo-3,4-dihydro-quinoxalin-2-yl)-6-hydroxy-indol-1-yl]propyl-ammonium acetate
FAB-MS: m/z 404 [MH+]

EXAMPLE 92

3-[2-Methyl-3-(6-nitro-3-oxo-3,4-dihydro-quinoxalin-2-yl)-indol-1-yl]propyl-ammonium acetate
FAB-MS: m/z 378 [MH+]

EXAMPLE 93

3-[5-Benzyloxy-3-(6-nitro-3-oxo-3,4-dihydro-quinoxalin-2-yl)-indol-1-yl]-propyl-ammonium acetate
FAB-MS: m/z 470 [MH+]

EXAMPLE 94

3-[5-Amino-3-(6-amino-3-oxo-3,4-dihydro-quinoxalin-2-yl)-indol-1-yl]-propyl-ammonium acetate
FAB-MS: m/z 349 [MH+]

EXAMPLE 95

3-[6-Nitro-3-(6-nitro-3-oxo-3,4-dihydro-quinoxalin-2-yl)-indol-1-yl]propyl-ammonium acetate
FAB-MS: m/z 409 [MH+]

EXAMPLE 96

3-[2-Ethyl-3-(6-nitro-3-oxo-3,4-dihydro-quinoxalin-2-yl)-indol-1-yl]-propyl-ammonium acetate
FAB-MS: m/z 392 [MH+]

EXAMPLE 97

3-[6-Benzyloxy-3-(6-nitro-3-oxo-3,4-dihydro-quinoxalin-2-yl)-indol-1-yl]propyl-ammonium acetate
FAB-MS: m/z 470 [MH+]

EXAMPLE 98

3-[5-Methoxycarbonyl-3-(6-nitro-3-oxo-3,4-dihydro-quinoxalin-2-yl)-indol-1-yl]propyl-ammonium acetate
FAB-MS: m/z 422 [MH+]

EXAMPLE 99

3-[2-Methyl-3-(5-methyl-3-oxo-3,4-dihydro-quinoxalin-2-yl)-indol-1-yl]propyl-ammonium acetate
FAB-MS: m/z 347 [MH+]

EXAMPLE 100

3-[5-Benzyloxy-3-(5-methyl-3-oxo-3,4-dihydro-quinoxalin-2-yl)-indol-1-yl]propyl-ammonium acetate
FAB-MS: m/z 439 [MH+]

EXAMPLE 101

3-[5-Amino-3-(5-methyl-3-oxo-3,4-dihydro-quinoxalin-2-yl)-indol-1-yl]propyl-ammonium acetate
FAB-MS: m/z 348 [MH+]

EXAMPLE 102

3-[3-(5-Methyl-3-oxo-3,4-dihydro-quinoxalin-2-yl)-6-nitro-indol-1-yl]propyl-ammonium acetate
FAB-MS: m/z 378 [MH+]

EXAMPLE 103

3-[2-(4-Chloro-phenyl)-3-(5-methyl-3-oxo-3,4-dihydro-quinoxalin-2-yl)-indol-1-yl]-propyl-ammonium acetate
FAB-MS: m/z 444 [MH+]

EXAMPLE 104

3-[6-Benzyloxy-3-(5-methyl-3-oxo-3,4-dihydro-quinoxalin-2-yl)-indol-1-yl]propyl-ammonium acetate
FAB-MS: m/z 439 [MH+]

EXAMPLE 105

3-[5-Methoxycarbonyl-3-(5-methyl-3-oxo-3,4-dihydro-quinoxalin-2-yl)-indol-1-yl]-propyl-ammonium acetate
FAB-MS: m/z 391 [MH+]

EXAMPLE 106

3-[5-Methoxycarbonyl-3-(5-methyl-3-oxo-3,4-dihydro-quinoxalin-2-yl)-indol-1-yl]propyl-ammonium acetate
FAB-MS: m/z 349 [MH+]

EXAMPLE 107

3-[3-(7-Methoxy-3-oxo-3,4-dihydro-quinoxalin-2-yl)-2-methyl-indol-1-yl]propyl-ammonium acetate
FAB-MS: m/z 363 [MH+]

EXAMPLE 108

3-[5-Benzyloxy-3-(7-methoxy-3-oxo-3,4-dihydro-quinoxalin-2-yl)-indol-1-yl]propyl-ammonium acetate
FAB-MS: m/z 455 [MH+]

EXAMPLE 109

3-[5-Amino-3-(7-methoxy-3-oxo-3,4-dihydro-quinoxalin-2-yl)-indol-1-yl]-propyl-ammonium acetate
FAB-MS: m/z 364 [MH+]

EXAMPLE 110

3-[3-(7-Methoxy-3-oxo-3,4-dihydro-quinoxalin-2-yl)-6-nitro-indol-1-yl]propyl-ammonium acetate
FAB-MS: m/z 394 [MH+]

EXAMPLE 11

3-[2-(4-Chloro-phenyl)-3-(7-methoxy-3-oxo-3,4-dihydro-quinoxalin-2-yl)-indol-1-yl]-propyl-ammonium acetate
FAB-MS: m/z 460 [MH+]

EXAMPLE 112

3-[2-Ethyl-3-(7-methoxy-3-oxo-3,4-dihydro-quinoxalin-2-yl)-indol-1-yl]-propyl-ammonium acetate
FAB-MS: m/z 377 [MH+]

EXAMPLE 113

3-[6-Benzyloxy-3-(7-methoxy-3-oxo-3,4-dihydro-quinoxalin-2-yl)-indol-1-yl]propyl-ammonium acetate
FAB-MS: m/z 455 [MH+]

EXAMPLE 114

3-[5-Methoxycarbonyl-3-(7-methoxy-3-oxo-3,4-dihydro-quinoxalin-2-yl)-indol-1-yl]-propyl-ammonium acetate
FAB-MS: m/z 407 [MH+]

EXAMPLE 115

3-[6-Hydroxy-3-(7-methoxy-3-oxo-3,4-dihydro-quinoxalin-2-yl)-indol-1-yl]-propyl-ammonium acetate
FAB-MS: m/z 365 [MH+]

EXAMPLE 116

3-[1-(3-Hydroxy-propyl)-1H-indol-3-yl]-1H-quinoxalin-2-one
FAB-MS: m/z 320 [MH+]

Example 117

Dimethyl-{3-[3-(1-methyl-1H-indol-3-yl)-2-oxo-2H-quinoxalin-1-yl]propyl}-ammonium trifluoroacetate
FAB-MS: m/z 361 [MH+]

EXAMPLE 118

3-{3-[4-(2-Hydroxy-ethyl)-3-oxo-3,4-dihydro-quinoxalin-2-yl]-indol-1-yl}propyl-ammonium acetate
FAB-MS: m/z 363 [MH+]

EXAMPLE 119

3-[2-Benzyl-1-(3-hydroxy-propyl)-1H-indol-3-yl]-1H-quinoxalin-2-one
FAB-MS: m/z 410 [MH+]

EXAMPLE 120

3-[2-Benzyl-3-(3-oxo-3,4-dihydro-quinoxalin-2-yl)-indol-1-yl]propyl-ammonium acetate
FAB-MS: m/z 409 [MH+]

EXAMPLE 121

3-[1-(3-Ammonium-propyl)-1H-indol-3-yl]-1,5-dimethyl-2-oxo-1,2-dihydro-pyrido[2,3-b]pyrazin-5-ium bistrifluoroacetate
FAB-MS: m/z 348 [MH+]

EXAMPLE 122

[3-(3-Oxo-3,4-dihydro-quinoxalin-2-yl)-indol-1-yl]-acetic acid tert-butyl ester
FAB-MS: m/z 376 [MH+]

EXAMPLE 123

[3-(3-Oxo-3,4-dihydro-quinoxalin-2-yl)-indol-1-yl]-acetic acid
FAB-MS: m/z 320 [MH+]

EXAMPLE 124

3-[2-Benzyl-1-(3-hydroxy-propyl)-1H-indol-3-yl]-1H-quinoxalin-2-one
FAB-MS: m/s 410 [MH+]

EXAMPLE 125

3-[2-Benzyl-3-(3-oxo-3,4-dihydro-quinoxalin-2-yl)-indol-1-yl]-propyl-ammonium acetate
FAB-MS: m/s 409 [MH+]

EXAMPLE 126

[3-(3-Oxo-3,4-dihydro-quinoxalin-2-yl)-indol-1-yl]-acetic acid tert butyl ester
FAB-MS: m/s 376 [MH+]

EXAMPLE 127

[3-(3-Oxo-3,4-dihydro-quinoxalin-2-yl)-indol-1-yl]-acetic acid
FAB-MS: m/s 320 [MH+]

EXAMPLE 128

3-[3-(3-Oxo-3,4-dihydro-benzo[g]quinoxalin-2-yl)-indol-1-yl]-propyl-ammonium acetate FAB-MS: m/s 369 [MH+]

The invention also provides the free bases of those of the above compounds which are exemplified as salts.

What is claimed is:
1. A compound of formula (IA):

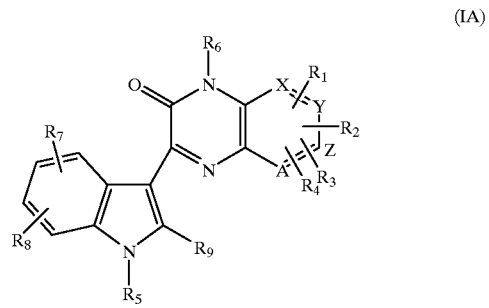

wherein X, Y, Z, and A is each independently carbon;

$R_1$, $R_2$, $R_3$, and $R_4$ is each independently H, amino, nitro, halo, $C_{1-6}$ alkyl, phenyl$C_{1-6}$ alkyl, $C_{1-6}$ alkoxy, halo$C_{1-6}$ alkyl, $C_{1-6}$ alkoxycarbonyl, or absent when the atom to which it would be attached is nitrogen;

$R_5$ and $R_6$ is each independently H, $C_{1-6}$ alkyl, hydroxy$C_{1-6}$ alkyl, amino$C_{1-6}$ alkyl, phenyl$C_{1-6}$ alkyl, carboxy$C_{1-6}$ alkyl, $C_{2-6}$ alkenyl, (phenyl$C_{1-3}$ alkoxy)$C_{1-3}$ alkyl, ($C_{1-6}$ acyloxy)$C_{1-6}$ alkyl, ($C_{1-6}$ alkoxycarbonyl)$C_{1-6}$ alkyl, (mono- or di-$C_{1-6}$ alkyl)amino$C_{1-6}$ alkyl, ($C_{1-6}$ alkyl)aminocarbonyl$C_{1-6}$ alkyl, ($C_{1-6}$ acylamino)$C_{1-6}$ alkyl, (amino$C_{1-3}$ alkylphenyl)$C_{1-3}$ alkyl, or aminodeoxyhexopyranosyl;

$R_7$ and $R_8$ is each independently H, amino, nitro, hydroxy, halogen, $C_{1-6}$ alkoxy, phenyl$C_{1-6}$ alkoxy or $C_{1-6}$ alkoxycarbonyl;

$R_9$ is H, $C_{1-6}$ alkyl, phenyl, halophenyl or phenyl$C_{1-6}$ alkyl;

or a pharmaceutically acceptable salt thereof, with the proviso that:
3-(1H-indol-3-yl)-1H-quinoxalin-2-one,
3-(2-methyl-1H-indol-3-yl)-1H-quinoxalin-2-one, and
3-(1,2-diphenyl-1H-indol-3-yl)-1H-quinoxalin-2-one
are excluded.

2. A compound according to claim 1, wherein at least one of $R_5$ and $R_6$ is amino $C_{1-6}$alkyl.

3. A compound according to claim 1, wherein at least one of Y and Z is substituted.

4. A compound according to claim 1, wherein at least one of Y and Z is substituted with halo, methoxy or alkoxycarbonyl.

5. A compound according to claim 1 wherein position 5 of the indole is substituted.

6. A compound according to claim 1 wherein $R_9$ is H or alkyl.

7. A compound according to claim 1 wherein $R_5$ or $R_6$ is an aminodeoxyhexpyranosyl.

8. A compound selected from the group consisting of:
3-[3-(4-Methyl-3-oxo-3,4-dihydro-quinoxalin-2-yl)-indol-1-yl]-propyl-ammonium acetate,
3-[3-(6,7-Dichloro-3-oxo-3,4-dihydro-quinoxalin-2-yl)-indol-1-yl]-propyl-ammonium acetate,
3-[3-(6,7-Dichloro-3-oxo-3,4-dihydro-quinoxalin-2-yl)-5-methoxycarbonyl-indol-1-yl]-propyl-ammonium acetate,
3-[3-(6,7-Dichloro-4-methyl-3-oxo-3,4-dihydro-quinoxalin-2-yl)-5-methoxycarbonyl-indol-1-yl]-propyl-ammonium acetate, 3-[5-Methoxycarbonyl-3-(7-methoxy-3-oxo-3,4-dihydro-quinoxalin-2-yl)-indol-1-yl]-propyl-ammonium acetate, 3-[3-(4-tert-Butoxycarbonylmethyl-7-methoxy-3-oxo-3,4-dihydro-quinoxalin-2-yl)-5-methoxycarbonyl-indol-1-yl]-propyl-ammonium acetate, 3-[3-(4-(3-Ammoniumpropyl)-3-oxo-3,4-dihydro-quinoxalin-2-yl)-indol-1-yl]-propyl-ammonium bis trifluoroacetate, Dimethyl-{3-[3-(1-methyl-1H-indol-3-yl)-2-oxo-2H-quinoxalin-1-yl]-propyl}-ammonium trifluoroacetate, 3-[6-Benzyloxy-3-(7-methoxy-4-methyl-3-oxo-3,4-dihydro-quinoxalin-2-yl)-indol-1-yl]-propyl-ammonium acetate, 3-[5-Benzyloxy-3-(4-tert-butoxycarbonylmethyl-7-methoxy-3-oxo-3,4-dihydro-quinoxalin-2-yl)-indol-1-yl]-propyl-ammonium acetate, 3-[2-(4-Chloro-phenyl)-3-(7-methoxy-3-oxo-3,4-dihydro-quinoxalin-2-yl)-indol-1-yl]-propyl-ammonium acetate, 3-[2-(4-Chloro-phenyl)-3-(7-methoxy-4-methyl-3-oxo-3,4-dihydro-quinoxalin-2-yl)-indol-1-yl]-propyl-ammonium acetate, 3-[3-(6,7-Dichloro-4-methyl-3-oxo-3,4-dihydro-quinoxalin-2-yl)-2-ethyl-indol-1-yl]-propyl-ammonium acetate, 3-[3-(5-Methyl-3-oxo-3,4-dihydro-quinoxalin-2-yl)-6-nitro-indol-1-yl]-propyl-ammonium acetate, 3-[6-Nitro-3-(6-nitro-3-oxo-3,4-dihydro-quinoxalin-2-yl)-indol-1-yl]-propyl-ammonium acetate, 4-[3-(3-Oxo-3,4-dihydro-quinoxalin-2-yl)-indol-1-ylmethyl]-benzyl-ammonium acetate, 3-[3-(4-Methyl-3-oxo-3,4-dihydro-quinoxalin-2-yl)-indol-1-ylmethyl]-benzyl-ammonium trifluoroacetate, and 3-[3-(4-Benzyl-3-oxo-3,4-dihydro-quinoxalin-2-yl)-indol-1-yl]-propyl-ammonium trifluoroacetate;

or a free amine.

9. A free amine of a compound according to claim 8.

10. A pharmaceutical composition comprising a compound according to claim 1 and a pharmaceutically acceptable carrier.

11. A compound of formula (II):

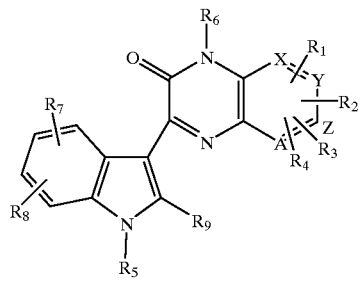

(II)

wherein X, Y, Z, and A is each independently carbon;

$R_1$, $R_2$, $R_3$, and $R_4$ is each independently H, hydroxy, amino, nitro, halo, $C_{1-6}$ alkyl, phenyl$C_{1-6}$ alkyl, $C_{1-6}$ alkoxy, halo$C_{1-6}$ alkyl, $C_{1-6}$ alkoxycarbonyl, or absent when the atom to which it would be attached is nitrogen;

$R_5$ and $R_6$ is each independently H, $C_{1-6}$ alkyl, hydroxy$C_{1-6}$ alkyl, amino$C_{1-6}$ alkyl, phenyl$C_{1-6}$ alkyl, carboxy$C_{1-6}$ alkyl, $C_{2-6}$ alkenyl, (phenyl$C_{1-3}$ alkoxy) $C_{1-3}$ alkyl, ($C_{1-6}$ acyloxy)$C_{1-6}$ alkyl, ($C_{1-6}$ alkoxycarbonyl)$C_{1-6}$ alkyl, (mono- or di-$C_{1-6}$ alkyl) amino$C_{1-6}$ alkyl, ($C_{1-6}$ alkyl)aminocarbonyl$C_{1-6}$ alkyl, ($C_{1-6}$ acylamino)$C_{1-6}$ alkyl, (amino$C_{1-3}$ alkylphenyl)$C_{1-3}$ alkyl, or aminodeoxyhexopyranosyl;

$R_7$ and $R_8$ is each independently H, amino, nitro, hydroxy, halogen, $C_{1-6}$ alkoxy, phenyl$C_{1-6}$ alkoxy or $C_{1-6}$ alkoxycarbonyl;

$R_9$ is H, $C_{1-6}$ alkyl, phenyl, halophenyl or phenyl$C_{1-6}$ alkyl;

and at least one of $R_5$ and $R_6$ carries a protected amino, carboxy or hydroxy group, or a compound of formula (III)

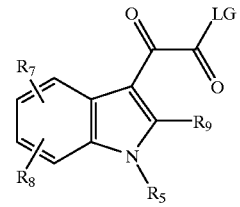

(III)

wherein $R_5$, $R_7$, $R_8$, and $R_9$ are as defined above, but when $R_5$ carries an amino, carboxy or hydroxy groups, such group is in a protected form; and LG is a leaving group.

* * * * *